United States Patent
Marzahl et al.

(10) Patent No.: US 11,854,191 B2
(45) Date of Patent: Dec. 26, 2023

(54) IMAGE PROCESSING METHOD FOR DISPLAYING CELLS OF A PLURALITY OF OVERALL IMAGES

(71) Applicant: EUROIMMUN Medizinische Labordiagnostika AG, Luebeck (DE)

(72) Inventors: Christian Marzahl, Erlangen (DE); Stefan Gerlach, Groß Groenau (DE); Joern Voigt, Luebeck (DE); Christine Kroeger, Ahrensboek (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 309 days.

(21) Appl. No.: 17/189,449

(22) Filed: Mar. 2, 2021

(65) Prior Publication Data

US 2021/0272279 A1  Sep. 2, 2021

(30) Foreign Application Priority Data

Mar. 2, 2020  (EP) ..................................... 20160329

(51) Int. Cl.
*G06T 7/00* (2017.01)
*G16H 30/40* (2018.01)
*G06F 18/2431* (2023.01)

(52) U.S. Cl.
CPC ........ *G06T 7/0012* (2013.01); *G06F 18/2431* (2023.01); *G16H 30/40* (2018.01);
(Continued)

(58) Field of Classification Search
CPC ......... G06T 7/0012; G06T 2207/10056; G06T 2207/30024; G06T 2207/30204; G06F 18/2431; G16H 30/40
See application file for complete search history.

(56) References Cited

U.S. PATENT DOCUMENTS

| | | | | |
|---|---|---|---|---|
| 6,652,456 | B2 * | 11/2003 | Gelfand | ............. G01N 15/1475 128/920 |
| 11,257,212 | B2 * | 2/2022 | Nagasaka | ................. G06T 7/00 |

(Continued)

OTHER PUBLICATIONS

Komura et al., "Machine Learning Methods for Histopathological Image Analysis", Computational and Structural Biotechnology Journal 16 (2018) pp. 34-42 (Year: 2018).*

(Continued)

*Primary Examiner* — Nay A Maung
*Assistant Examiner* — Jose M Torres
(74) *Attorney, Agent, or Firm* — Bochner PLLC; Andrew D. Bochner

(57) ABSTRACT

An image processing method is provided for displaying cells from a plurality of pathology images or overall images. A respective overall image represents a respective patient tissue sample or a respective patient cell sample. The method includes the steps of: providing the overall images, detecting individual cell images in the overall images by means of a computer-assisted algorithm, determining classification data by means of the computer-assisted algorithm, wherein the classification data indicate a respective unique mapping of a respective detected cell image to one of a plurality of cell classes, and wherein the classification data further have a respective measure of confidence in respect of the respective unique mapping, generating respective class images for the respective cell classes, wherein a class image of a cell class reproduces the cell images mapped to the cell class in a regular arrangement and with a predetermined order, and wherein further the order of the mapped cell images is chosen on the basis of the measures of confidence of the mapped cell images, and further, displaying a portion of at least one class image.

9 Claims, 14 Drawing Sheets

(52) U.S. Cl.
CPC ............... *G06T 2207/10056* (2013.01); *G06T 2207/30024* (2013.01); *G06T 2207/30204* (2013.01)

(56) References Cited

U.S. PATENT DOCUMENTS

| | | | | |
|---|---|---|---|---|
| 11,594,056 B2* | 2/2023 | Wakui | ................... | G06V 30/413 |
| 2002/0106119 A1* | 8/2002 | Foran | ..................... | G16H 30/20 |
| | | | | 382/133 |
| 2004/0167806 A1* | 8/2004 | Eichhorn | ............... | G02B 21/26 |
| | | | | 382/133 |
| 2006/0050948 A1 | 3/2006 | Sumida et al. | | |
| 2008/0166035 A1* | 7/2008 | Qian | .................... | G06V 20/698 |
| | | | | 382/133 |
| 2012/0314049 A1* | 12/2012 | Gu | ........................ | G02B 21/365 |
| | | | | 348/79 |
| 2013/0002847 A1 | 1/2013 | Zahniser et al. | | |
| 2013/0101199 A1* | 4/2013 | Alexandrov | ......... | G06V 20/695 |
| | | | | 382/133 |
| 2015/0004630 A1* | 1/2015 | Lange | .................. | G06V 20/698 |
| | | | | 435/40.52 |
| 2016/0078276 A1 | 3/2016 | Bengtsson et al. | | |
| 2019/0180147 A1* | 6/2019 | Zhang | ................. | G06F 18/2413 |
| 2020/0300764 A1 | 9/2020 | Gerlach et al. | | |
| 2021/0019883 A1 | 1/2021 | Krauth et al. | | |
| 2021/0035678 A1* | 2/2021 | Corvo | ................... | G06T 11/206 |

OTHER PUBLICATIONS

Girshick, Ross et al., "Rich feature hierarchies for accurate object detection and semantic segmentation," 2014 IEEE Conference on Computer Vision and Pattern Recognition, 2014, pp. 580-587.

Lin Tsung-Yi et al., "Focal Loss for Dense Object Detection," in Proceedings of the IEEE International Conference on Computer Vision, 2017, pp. 2980-2988.

Liu, Wei et al., "SSD: Single Shot MultiBox Detector," ECCV 2016, Part I, LNCS 9905, 2016, pp. 21-37.

Redmon, Joseph et al., "Yolo9000: Better, Faster, Stronger," arXiv:1612.08242, Dec. 25, 2016, pp. 9.

Ren, Shaoqing et al., "Faster R-CNN: Towards realtime object detection with region proposal networks," arXiv preprint arXiv:1506.01497, Jun. 4, 2015, pp. 9.

Sermanet, Pierre et al., "Overfeat: Integrated recognition, localization and detection using convolutional networks," arXiv:1312.6229, 2013, pp. 16.

Shen, Zhiqiang et al., "DSOD: Learning deeply supervised object detectors from scratch," in Proceedings of the IEEE International Conference on Computer Vision, 2017, pp. 1919-1927.

\* cited by examiner

GB1

GB11

KL1 — macrophages — GW1
KL2 — lymphocytes — GW2
KL3 — eosinophils — GW3

LG

KB1

GB21

GB22

KB100

TA100

TA200

IMAGE PROCESSING METHOD FOR DISPLAYING CELLS OF A PLURALITY OF OVERALL IMAGES

CROSS-REFERENCE TO RELATED APPLICATIONS

The present application claims priority pursuant to 35 U.S.C. § 119(a) to EP patent application 20160329.7, filed Mar. 2, 2020, which is incorporated by reference herein in its entirety.

BACKGROUND

The invention relates to an image processing method for displaying cells of a plurality of overall images. The invention further relates to an image processing method to be carried out on a server, an image processing method to be carried out on a client, and corresponding computer program products to be executed on a computer for the purposes of carrying out the methods on the server and the client, respectively.

An essential task of a pathologist within the scope of pathological examinations lies in analyzing a plurality of overall images, an overall image representing a patient tissue sample in the form of a tissue section or an overall image representing a patient cell sample in the form of a smear of a liquid patient sample. Such an analysis of overall images within the scope of a pathological examination is usually implemented as follows: the pathologist maps the represented individual cells or cell images to different cell classes in at least a plurality of segments of each overall image and then counts the number of cells occurring in the class for each cell class. The pathologist bases their findings on the respective number of cells in a respective cell class. Within the scope of the examination, it is typically not only a single overall image that is analyzed by the pathologist in the manner described above but a plurality of overall images, which can be traced back to patient samples from the same patient. For findings on the basis of overall images, which are present as tissue sections, it is conventional, for example, for a pathologist to analyze a plurality of segments as so-called high-power fields in respect of the number of cells of the mitosis cell class present in the overall image, with a high-power field reproducing a segment of the overall image with an area of 0.1 to 0.4 mm$^2$ and typically 50 high-power fields of an overall image or a tissue section being analyzed.

A single overall image has a very large number of individual cell images and so the pathologist must simultaneously observe a very large number of cells of different cell classes to acquire a high-power field, even with the possibility of a substantial optical magnification of the overall image using a microscope or, for example, using a digital display unit such as a computer monitor, in order to map the cells to the cell classes and determine the respective cell count for each cell class. If a pathologist observes a certain image section of an overall image, they see respective cells of different cell classes at respective spatial positions, as has emerged on account of the spatial structure of the sample.

Within the scope of the pathological examination of one or more overall images, it is further conventional for such an examination to be carried out or for such findings to be made not only by a single pathologist but for this to be checked again and corrected where necessary by a further, second pathologist. Cell class mappings implemented by a first pathologist can then be altered or corrected by the second pathologist where necessary.

The overall images each represent a patient tissue sample in the form of a tissue section or the overall images each represent a patient cell sample in the form of a smear of a liquid patient sample. For overall images that each represent a patient tissue sample in the form of a tissue section, a first cell class is the mitosis cell class and a second cell class is the non-mitosis cell class. For overall images that each represent a patient cell sample in the form of a smear of a liquid patient sample, a first cell class is the macrophage class, a second cell class is the lymphocyte class and a third cell class is the eosinophil class.

In the case where the overall images each represent a patient tissue sample in the form of a tissue section, there are at least two cell classes, including the mitosis cell class as a first cell class and the non-mitosis cell class as a second cell class. In the case where the overall images each represent a patient cell sample in the form of a smear of a liquid patient sample, there are at least two cell classes, selected from the group of the macrophage class, the lymphocyte class and the eosinophil class.

SUMMARY

It is an object of the invention to provide an image processing method for displaying cells of a plurality of overall images, in which a classification result in respect of individual cell images and a cell count for respective cell classes for the plurality of overall images can be particularly reliably checked in computer-assisted fashion by the pathologist.

The object according to the invention is solved by the proposed image processing method for displaying cells of a plurality of overall images.

Here, a respective overall image represents a respective patient tissue sample or a respective patient cell sample, in particular an image of a smear of a liquid patient cell sample.

The overall images are provided first. Then, individual cell images are detected in the overall images by means of a computer-assisted algorithm, for example a neural network. Further, classification data are determined by means of the computer-assisted algorithm. The classification data indicate a respective unique mapping of a respective detected cell image to one of a plurality of cell classes. Further, the classification data have a respective measure of confidence in respect of the respective unique mapping of a detected cell image to one of the plurality of cell classes. Thus, cells of the same class are mapped to the same class image.

Further, respective class images are generated for the respective cell classes. Herein, a class image of a cell class reproduces the cell images mapped to the cell class in a regular arrangement and with a predetermined order. The predetermined order is chosen on the basis of the measures of confidence of the mapped cell images of the class image or the corresponding cell class. Preferably, the order starts with the cell image with the greatest measure of confidence, followed by further cell images with corresponding decreasing measures of confidence. Finally, at least one portion of at least one class image is displayed. Preferably, a user can modify and thus correct a mapping of a cell image to a cell class or the corresponding class image by way of a user input, preferably on the client. Preferably, a plurality of portions of a plurality of class images are displayed successively in time or in a time-sequential fashion.

The proposed image processing method according to the invention has different possible advantages, which will now be explained in more detail below.

By means of the computer-assisted algorithm, individual cell images are detected in the overall images and then mapped to different cell classes. If only one overall image of a tissue sample or cell sample were provided with optical markings corresponding to the cell classes and then displayed, with the respective spatial arrangements of the respective individual cell images remaining unchanged, it would be possible, in principle, for this to lead the pathologist to overall visual information that may be difficult to comprehend for a user or pathologist.

In this respect, FIG. 8 shows an overall image GB1 in exemplary fashion, in this case of a patient cell sample in the form of a smear. Further exemplary patient cell samples in the form of smears are illustrated in FIGS. 9A and 9B as overall images GB2 and GB3, respectively. FIG. 10A shows a classification result of the patient cell sample from FIG. 8 as an overall image GB11, in which small rectangles in different greys for different cell classes respectively indicate the classification results of individual detected cells or individual detected cell images. In this respect, FIG. 10B shows exemplary cell classes KL1, KL2, KL3 such as macrophages, lymphocytes or eosinophils, which are represented as rectangles with corresponding greyscale values GW1, GW2, GW3 in image GB11. In this form of presentation according to the prior art, there is a large amount of visual overall information for a pathologist. Although, in theory, a very strong optical magnification could be applied to the overall image GB11 such that the pathologist could then observe this overall image GB11 section-by-section in order to check and possibly correct the classification results of the computer-assisted algorithm, the pathologist would then precisely need to observe and check cells of different cell classes at the same time when observing a corresponding magnified section, with the spatial arrangement of the cells depending on the structure of the sample.

FIG. 11 shows a class image KB1 according to the invention, which shows detected individual cell images from the plurality of overall images GB1, GB2, GB3 for a certain individual cell class, which corresponds to the class image. Expressed differently, the class image KB1 depicts only those individual cell images belonging to an individual cell class, in a regular arrangement or regular spatial arrangement. Further, the order of the mapped cell images of the class image KB1 is chosen on the basis of the measures of confidence of the mapped cell images. By way of example, the cell image for which the computer-assisted algorithm has determined the greatest measure of confidence in respect of the mapping of this individual cell image to the class image KB1 or to the associated cell class can be arranged in the top left corner of the class image KB1. By way of example, the cell images can then be ordered from left to right with a decreasing measure of confidence in the top line, with this spatial regular arrangement being continued in the second line following next. Expressed differently, a class image KB1 corresponds to a matrix as a regular spatial arrangement of individual cell images.

FIG. 12A shows an exemplary portion TA1 with 10×8 individual detected cell images Z, Z1, Z2, Z3 of the same class image or the same cell class. The pathologist can then observe this portion of a class image and check the mapping of the individual cell images Z to the corresponding class image or the corresponding cell class by way of a visual inspection thereof. Thus, it is not the entire class image but only a portion that is displayed, and so the display means to be utilized can depict the cell images Z of the portion with sufficient magnification.

An advantage of the method according to the invention lies in the fact that only those individual cell images which were mapped to the same cell class by the computer-assisted method are now displayed for the pathologist when the latter observes the portion TA1 of the class image KB1. Further, the order of the individual cell images in the class image KB1 chosen according to the invention inherently represents information for the pathologist in respect of the individual cell images for which the algorithm has determined a high measure of confidence in respect of the respective mapping of the cell image to the cell class. Then, the pathologist can therefore start observing the individual cell images in the top left corner in order to check the mapping of the cell images to the cell class of the class image KB1 depicted here. The pathologist need not simultaneously observe a plurality of individual cell images of different classes in a random spatial arrangement—as can be seen in FIG. 10A—and then check by way of a visual inspection whether the mapping of cells to the respective cell class undertaken by the computer-assisted algorithm is correct. When observing the portion TA1, they can concentrate on a single cell class in this case. Further, on account of the position of a cell image Z in the class image or the portion TA1, they can grasp how certain the computer-assisted algorithm was when mapping a cell image to the corresponding class since cell images with a high measure of confidence are situated in different image regions to cell images with low measures of confidence. Therefore, from the position of a cell image, the pathologist can deduce how much they can trust the mapping of a cell image to the corresponding cell class by the computer-assisted algorithm.

Thus, the pathologist can be considered to be a user who, on account of the solution according to the invention, can particularly efficiently and quickly carry out the technical task of checking a mapping of cell images to cell classes. This aspect of efficiently and quickly carrying out a task by a user when displaying images can be considered analogous to the method for displaying images from the decision of the European Patent Office T0642/00; see the European patent application number 93300749.4, which is incorporated by reference herein in its entirety.

FIG. 14 illustrates yet again in a different way a possible advantage of the proposed image processing method. Individual cell images can be detected and classified from the plurality of overall images GB11, GB12, GB13; for example, into two different classes—class 1 and class 2—in this case. Then, a corresponding class image KB11, KB12 is generated for each of the cell classes. Then, a portion of a class image is displayed. Thus, when observing a portion thereof, the pathologist can observe together and at the same time a plurality of cell images from a plurality of overall images in respect of the mapping of the cell images to a certain cell class. Further, when displaying portions of different class images KB11, KB12, preferably temporally sequentially in succession, the pathologist can then check cell images of different cell classes in succession, while, however, always only having to check cell images of a single class in an individual portion.

Advantageous embodiments of the invention are subject matter of the dependent claims and are more particularly elucidated in the following description with some reference to the drawing.

Preferably, the aforementioned provision, detection, determination and generation steps are implemented on a server. The method further preferably includes the following steps: generating an annotation data record on the server, said annotation data record indicating for each class image respective mappings of the respective cell images to a cell class corresponding to the class image and further indicating respective local positions of the respective cell images within the class images, requesting a portion of a class image by a client, transmitting the portion and further at least one partial annotation data record corresponding to the portion from the server to the client and temporarily storing the partial annotation data record on the client, generating respective optical markings for respective cell images of the portion on the basis of at least the partial annotation data record on the client, wherein the respective optical markings indicate respective mappings of the respective cell images to a cell class corresponding to the class image, and displaying the portion and the associated optical markings on a display unit on the client.

Preferably, the method further includes the steps of: receiving a user input on the client, said user input indicating a selection of a displayed cell image and further indicating a new mapping of the selected cell image to a modified cell class, generating and displaying on the client a new optical marking for the selected cell image corresponding to the modified cell class, modifying the temporarily stored partial annotation data record in correspondence with the selected cell image and the modified cell class on the client, transmitting information from the client to the server indicating the selected cell image and the modified cell class, and modifying the annotation data record on the server in correspondence with the selected cell image and the modified cell class.

Preferably, the portion is a first portion. Preferably, the method further includes the steps of: requesting a second portion of the class image by the client, transmitting the second portion and further at least one second partial annotation data record corresponding to the second portion from the server to the client and temporarily storing the second partial annotation data record on the client, generating respective optical markings for respective cell images of the second portion on the basis of at least the second partial annotation data record on the client, wherein the respective optical markings indicate respective mappings of the respective cell images to a cell class corresponding to the class image, and displaying the second portion and associated optical markings on the client.

Preferably, the method further includes the steps of: receiving a synchronization request, and synchronizing the classification data with the modified annotation data record on the server.

Further proposed is an image processing method to be carried out on a server, including the steps of: providing a plurality of overall images, wherein a respective overall image represents a respective patient tissue sample or a respective patient cell sample, detecting individual cell images in the overall images by means of a computer-assisted algorithm, determining classification data by means of the computer-assisted algorithm, wherein the classification data indicate a respective unique mapping of a respective detected cell image to a respective cell class, and wherein the classification data further have a respective measure of confidence in respect of the respective unique mapping, generating respective class images for the respective cell classes, wherein a class image of a cell class of the cell images mapped to the cell class is chosen in a regular arrangement and with a predetermined order of the mapped cell images on the basis of the measures of confidence of the mapped cell images, generating an annotation data record, said annotation data record indicating for each class image respective mappings of the respective cell images to a cell class corresponding to the class image and further indicating respective local positions of the respective cell images within the class images, transmitting a portion of at least one class image and further at least one partial annotation data record corresponding to the portion to a client, receiving information from the client indicating a selected cell image and a modified cell class, and modifying the annotation data record in correspondence with the selected cell image and the modified cell class.

The image processing method to be carried out on a server further preferably includes the steps of: receiving a synchronization request, and synchronizing the classification data with the modified annotation data record.

Further proposed is an image processing method to be carried out on a client, including the steps of: requesting a portion of at least one class image from a server, wherein a class image reproduces cell images mapped to a cell class in a regular arrangement and with a predetermined order, receiving the portion of the class image and further at least one partial annotation data record corresponding to the portion from the server and temporarily storing the partial annotation data record, wherein the partial annotation data record for the portion of the class image indicates respective mappings of respective cell images to a cell class corresponding to the class image and wherein the partial annotation data record indicates respective local positions of the respective cell images within the class image, generating respective optical markings for respective cell images of the portion on the basis of at least the partial annotation data record, wherein the respective optical markings indicate respective mappings of the respective cell images to a cell class corresponding to the class image, and displaying the portion and associated optical markings of cell images of the portion.

The image processing method to be carried out on a client further preferably includes the steps of: receiving a user input, said user input indicating a selection of a displayed cell image and further indicating a new mapping of the selected cell image to a modified cell class, generating and displaying a new optical marking for the selected cell image corresponding to the modified mapped cell class, modifying the temporarily stored partial annotation data record in correspondence with the selected cell image and the modified cell class, and transmitting information to the server indicating the selected cell image and the modified cell class.

Further proposed is a computer program product comprising commands which, when the program is executed by a computer in the form of a server, prompt the latter to carry out the image processing method on a server.

Further proposed is a computer program product comprising commands which, when the program is executed by a computer in the form of a client, prompt the latter to carry out the image processing method on a client.

BRIEF DESCRIPTION OF THE DRAWINGS

Without restricting the general concept of the invention, the invention will be discussed in more detail below on the basis of specific embodiments with reference to the figures, in which.

DETAILED DESCRIPTION

Figure 1:
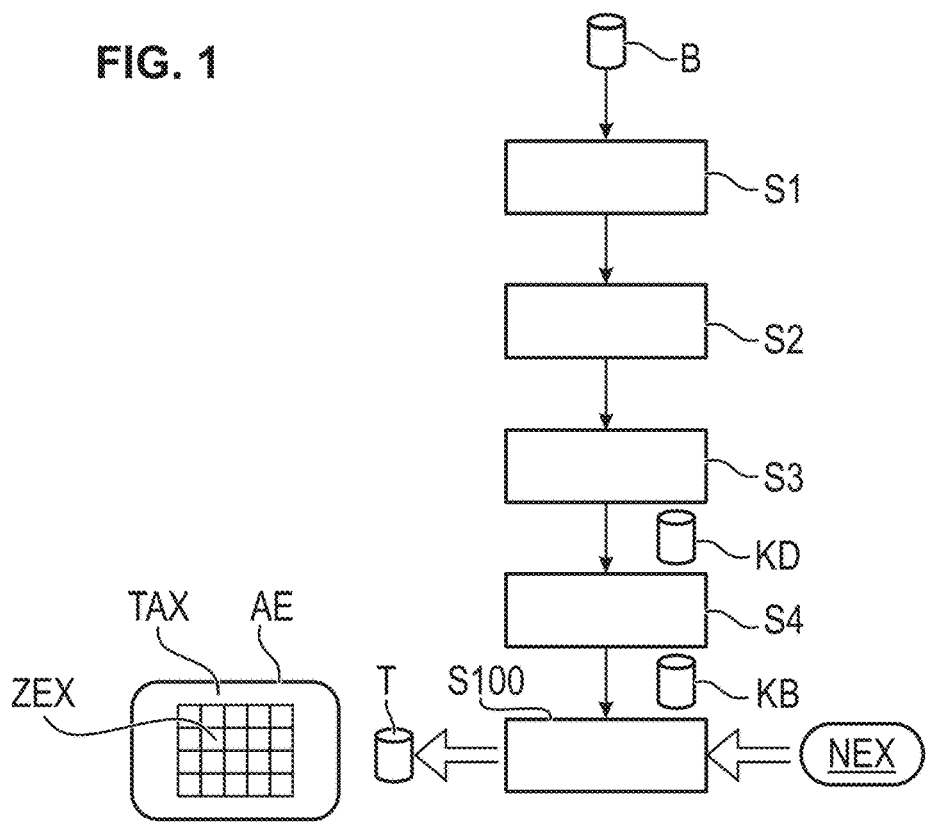
FIG. 1 shows steps for carrying out the image processing method according to the invention for displaying cells of a plurality of overall images in a portion of a class image.
Figure 8:
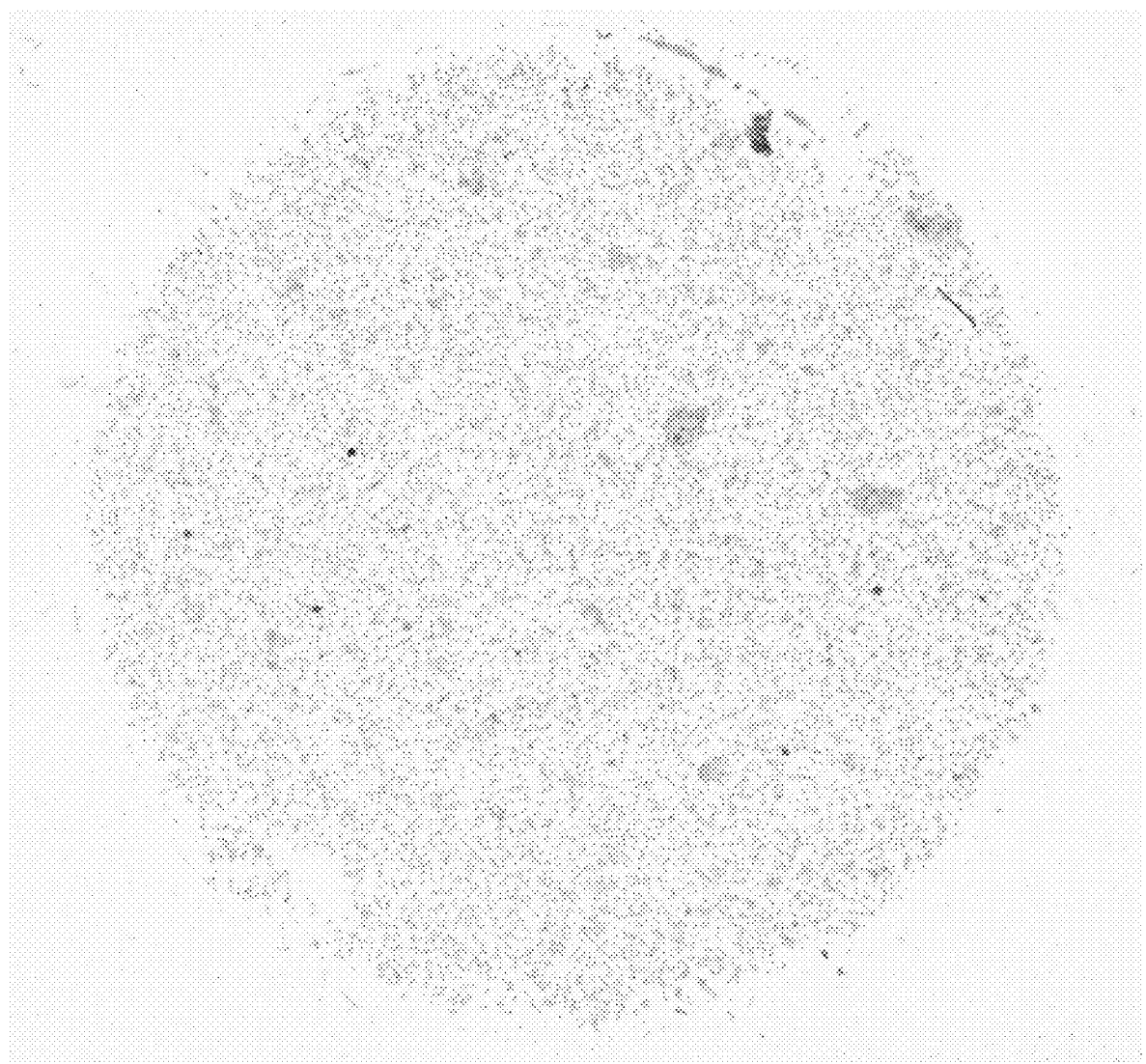
FIGS. 8, 9A and 9B show exemplary overall images.
Figure 9A:
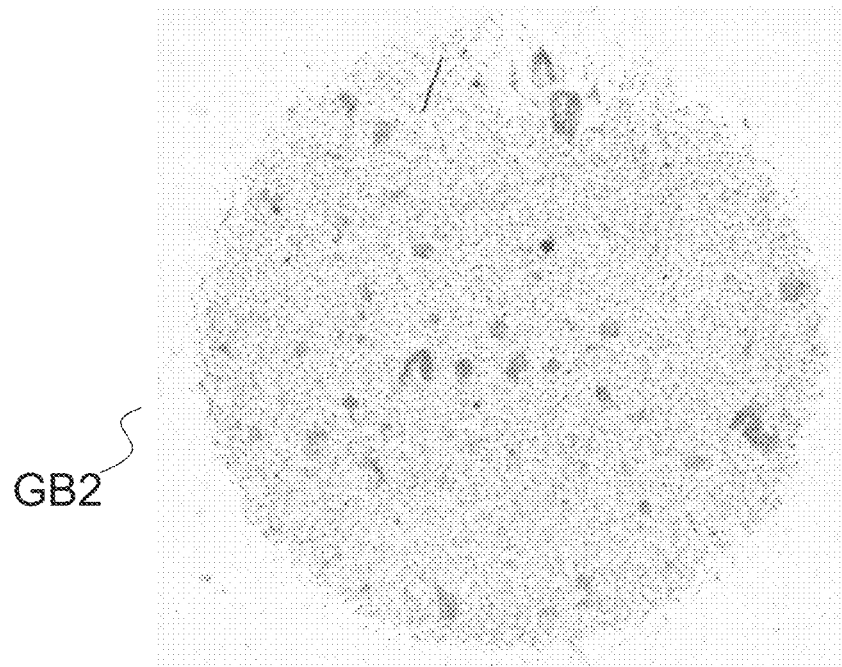
Figure 9B:
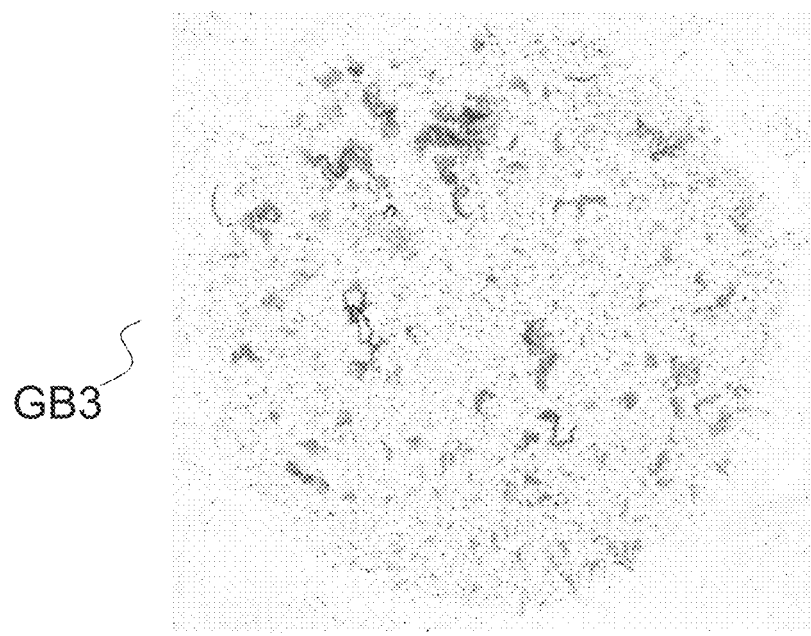

FIG. 1 illustrates a preferred sequence of steps for carrying out the image processing method according to the invention. In a step S1, the overall images are provided as image data B, for example the overall images GB1, GB2, GB3 from FIGS. 8, 9A and 9B. In a step S2, individual cell images are detected in the overall images by means of a computer-assisted algorithm such as a neural network, for example. In a step S3, classification data KD are determined by means of the computer-assisted algorithm. The classification data KD indicate a respective unique mapping of a respective detected cell image to one of a plurality of cell classes. Further, for a respective detected cell image, the classification data KD have a respective measure of confidence in respect of the respective unique mapping of the detected cell image to one of the plurality of cell classes.

Figure 11:
FIG. 11 shows an exemplary class image.

In a step S4, respective class images or class image data KB are generated for the respective cell classes, wherein a class image of a cell class reproduces the cell images mapped to the cell class in a regular arrangement with a predetermined order. An example of a class image is the class image KB1 in FIG. 11.

Figure 12A:
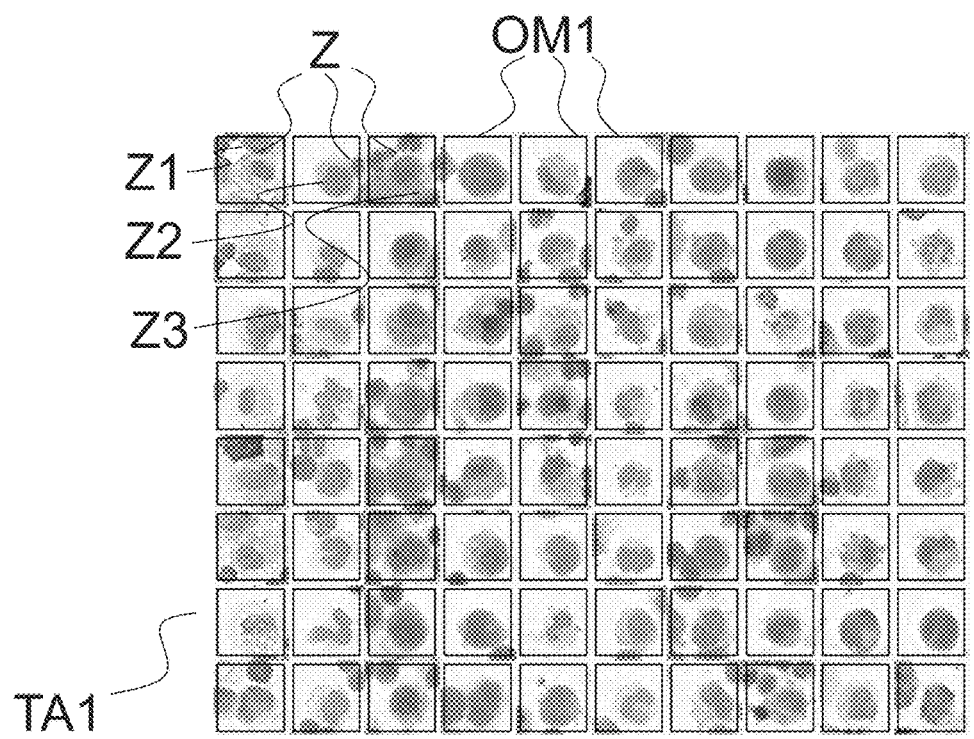
FIG. 12A shows a portion of a class image.

Then, in a step S100, a portion TAX of a class image is displayed, for example the portion TA1 of FIG. 12A. Thus, a portion TAX in the form of portion data T is output to a display unit AE, preferably of a client.

Figure 2:
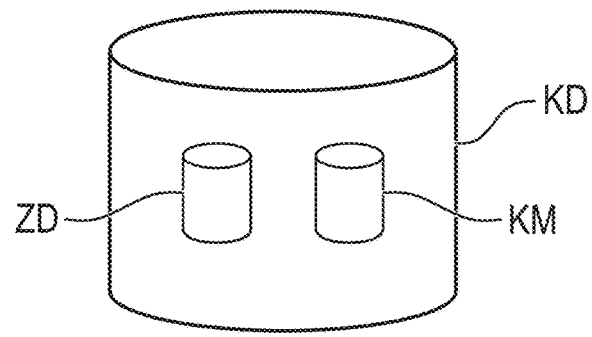
FIG. 2 shows exemplary data of measures of confidence.

FIG. 2 shows a preferred embodiment of classification data KD, which have mapping data ZD which in turn indicate respective unique mappings of respective detected cell images to cell classes. Further, the classification data KD have measure of confidence data KM which indicate a respective measure of confidence for a respective detected cell image in respect of the respective unique mapping of the detected cell image to one of a plurality of cell classes.

Figure 3:
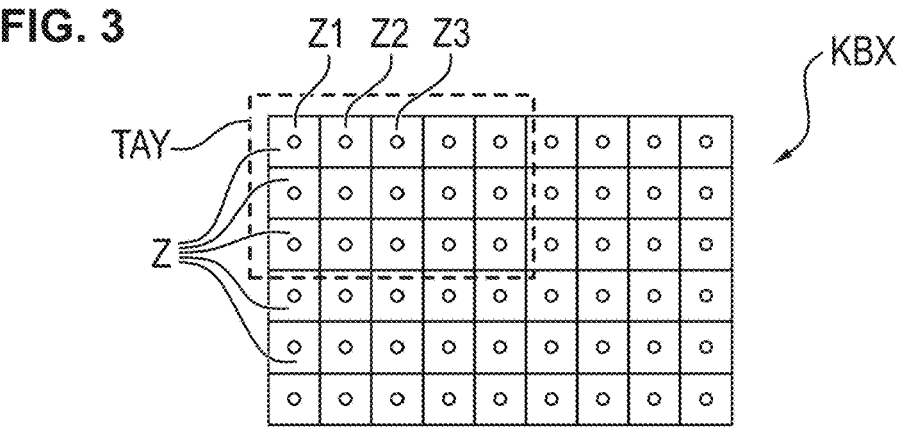
FIG. 3 shows an exemplary class image.

FIG. 3 shows an exemplary class image KBX with a regular spatial arrangement of individual cell images Z. A portion TAY is illustrated by means of a dashed rectangle. Here, the cell images Z are arranged in a predetermined order which is chosen on the basis of the measures of confidence of the corresponding cell images Z. By way of example, the cell image Z1 has the highest measure of confidence, the following cell image Z2 has the next higher measure of confidence, etc.

As already described above, the advantage of the proposed image processing method consists in that a pathologist need not observe the individual cell images detected in a plurality of overall images GB1, GB2, GB3 in the spatial arrangements as given in the overall image GB11, for example but instead said pathologist is shown in the portion TAY or in the portion TAX only cell images from a certain individual cell class of the class image KBX.

Preferably, steps S1 to S4 are carried out on a server and step S100 is carried out on a client.

Preferably, a user can modify and thus correct a mapping of a cell image ZEX to a cell class by way of a user input NEX, preferably on the client.

For the task of detecting individual cell images in the overall images by means of a computer-assisted algorithm and determining the classification data by means of the computer-assisted algorithm, the neural network according to T. Lin, P. Goyal, R. Girshick, K. He and P. Dollár, "Focal Loss for Dense Object Detection," in IEEE Transactions on Pattern Analysis and Machine Intelligence, vol. 42, no. 2, pp. 318-327, 1 Feb. 2020 (incorporated by reference herein in its entirety) is a suitable computer-assisted algorithm. This algorithm was used to generate the examples illustrated here.

Alternative algorithms for neural networks for solving the task of detecting individual cell images in the overall images by means of a computer-assisted algorithm and of determining the classification data by means of the computer-assisted algorithm are found in the following publications, each of which is incorporated by reference herein its entirety:

P. Sermanet, D. Eigen, X. Zhang, M. Mathieu, R. Fergus, and Y. LeCun, "Overfeat: Integrated recognition, localization and detection using convolutional networks," arXiv:1312.6229, 2013;

R. Girshick, J. Donahue, T. Darrell, and J. Malik, "Rich feature hierarchies for accu-rate object detection and semantic segmentation," in CVPR, 2014;

S. Ren, K. He, R. Girshick, and J. Sun, "Faster r-cnn: Towards realtime object detec-tion with region proposal networks," in NIPS, 2015, pp. 91-99;

J. Redmon and A. Farhadi, "Yolo9000: better, faster, stronger," arXiv:1612.08242, 2016;

W. Liu, D. Anguelov, D. Erhan, C. Szegedy, S. Reed, C.-Y. Fu, and A. C. Berg, "Ssd: Single shot multibox detector," in ECCV, 2016; and Z. Shen, Z. Liu, J. Li, Y. G. Jiang, Y. Chen, and X. Xue, "Dsod: Learning deeply super-vised object detectors from scratch," in ICCV, 2017.

Figure 4:
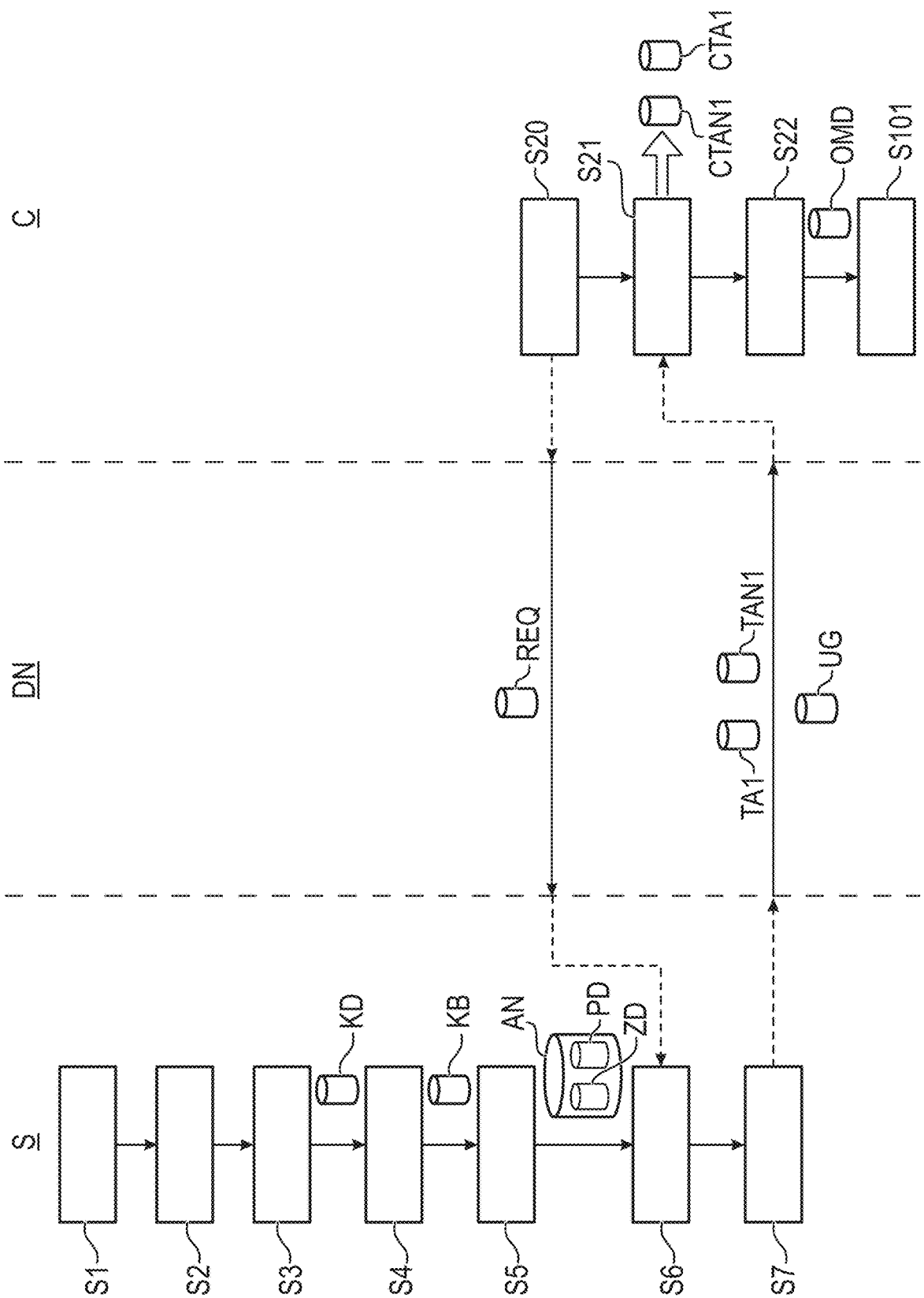
FIG. 4 shows preferred steps for carrying out the image processing method.

FIG. 4 shows further preferred steps of the proposed image processing method according to a preferred embodiment. Initially, steps S1, S2, S3 and S4 are carried out on the server side or on a server, as explained above in relation to FIG. 1. An annotation data record AN is then generated on the server in a step S5. The annotation data record AN has a mapping data record ZD which indicates for each class image a respective mapping of the respective cell images to a cell class corresponding to the class image. The annotation data record AN further has position data PD, which indicate respective local positions of the respective cell images within the class images.

In a step S6, the server awaits a request from a client. In a step S20, the client C requests a portion of a class image. The client C carries this out by transmitting or sending a request notification or a request data record REQ to the server S via a data network DN.

Upon reception of the request data record or the request notification REQ, the server S switches to step S7. In step S7, server S transmits the portion TA1 of a class image and, further, at least one partial annotation data record TAN1 corresponding to the portion TA1 to the client C as part of the annotation data record AN. In a step S21, the client C receives the portion TA1 and the partial annotation data record TAN1 and stores the partial annotation data record as temporary partial annotation data record CTAN1. Further, in step S21, the client preferably stores the portion TA1 as temporarily stored portion CTA1.

In a step S22, the client C generates optical markings in the form of an optical marking data record OMD. The optical marking data record OMD has respective optical markings for respective cell images of the portion CTA1 on the basis of at least the partial annotation data record CTAN1. The respective optical markings indicate a respective mapping of the respective cell images to a cell class corresponding to the class image.

In an alternative embodiment, the server S preferably transmits not only the partial annotation data record TA1, which belongs to the portion TA1, in step S7 but already the overall annotation data record AN. As a result thereof, it is precisely also at least that partial annotation data record TAN1 which corresponds to the transmitted portion TA1 that is transmitted from the server to the client.

In a step S101, the portion TA1 or CTA1 then is displayed on the client together with the associated optical markings.

The preferred exemplary embodiment of the proposed image processing method described here is advantageous, in particular, because a client system C can be used by a user or pathologist in order to be able to check an mapping of cell images to cell classes without all detected cell images of all class images having to be immediately transmitted to the client at once. A totality of all class images represents a very large amount of data, the transmission of which from a server to a client over a data network possibly taking up a significant amount of time. If a user or a pathologist wishes to use a client system C in order to call and then check image data and classification results or mapping results of an algorithm from a server S via a data network DN, the proposed method according to the embodiment highlighted here is advantageous since merely only a portion TA1 of a class image is initially transmitted and then displayed. If the totality of the image data of all class images were transferred ad hoc at once from the server S to the client C via the data network DN, this would require a significant amount of time and consequently mean a significant delay or latency for the pathologist when checking the class mappings of cell images at the client C.

A protocol of data processing in a distributed system of a client and server is thus proposed, wherein, in relation to a technical purpose, it should be noted that the server is responsible of generating optical markings. Thus, generation of the optical marking is only brought about on the client and hence at the location where the optical markings are used and displayed, and so the server itself need not generate these optical markings for all of the cell class images but the client precisely only needs to carry this out for the received portion on the basis of the partial annotation data record. Thus, what is taken into account is that computational resources for the generation of optical markings are only available to a limited extent and are only called or used at the client to the extent that this is also necessary for the subsequent display in relation to the corresponding portion.

As described above, FIG. 11 shows an exemplary class image KB1 of an individual cell class, in this case the macrophage class.

FIG. 12A shows an exemplary portion TA1 with 10×8 individual detected cell images Z, which are marked by the same optical marking OM1. Then, the pathologist can observe this portion and by way of a visual inspection examine the individual cell images Z in respect of their class mapping.

Figure 12B:
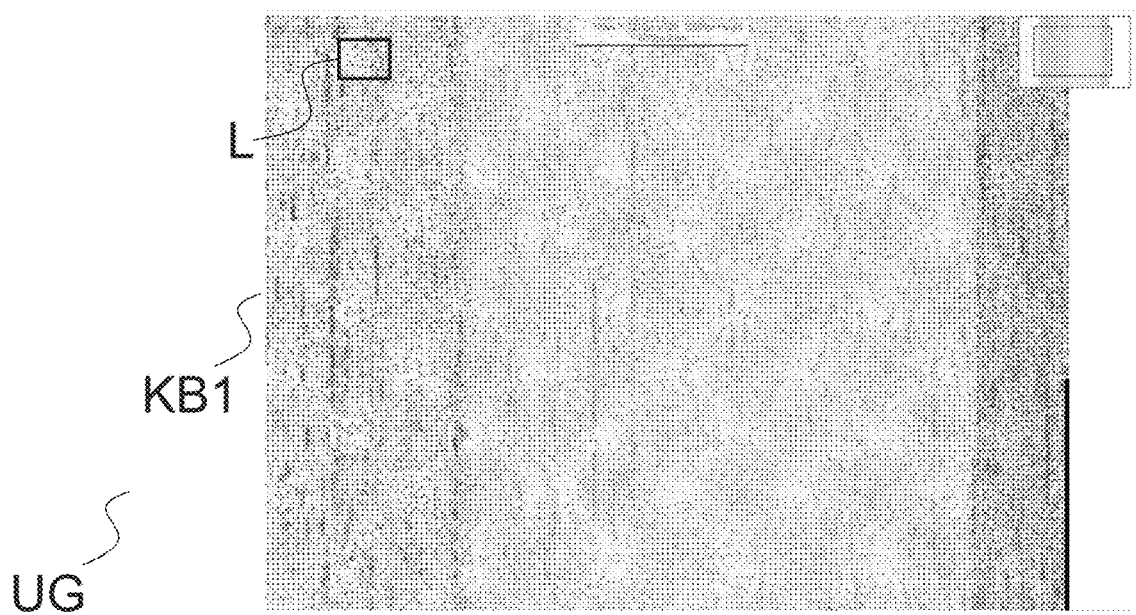
FIG. 12B shows an exemplary relative position of a portion within the class image of FIG. 11.

Preferably, an overview graphic UG of the class image KB1 with a reduced resolution is further transmitted from the server S to the client C via the data network DM in step S7 and is then displayed on the client side in step S101. Such an overview graphic UG, as illustrated in FIG. 12B, can then also by way of a relative position marking L indicate to the user or the pathologist the region of the class image KP1 from which the portion TA1 originates. As a result, the information as to whether the measures of confidence for the mapping of the cell images to the corresponding cell class were rather high or rather low is advantageously transmitted to the user by way of displaying the overview graphic of the class image KB1 and the relative position marking L even if only a portion TA1 of FIG. 12A is displayed since, of course, cell images mapped to the cell class or the class image KB1 are arranged in an order which is chosen on the basis of the measures of confidence of the mapping.

Figure 5:
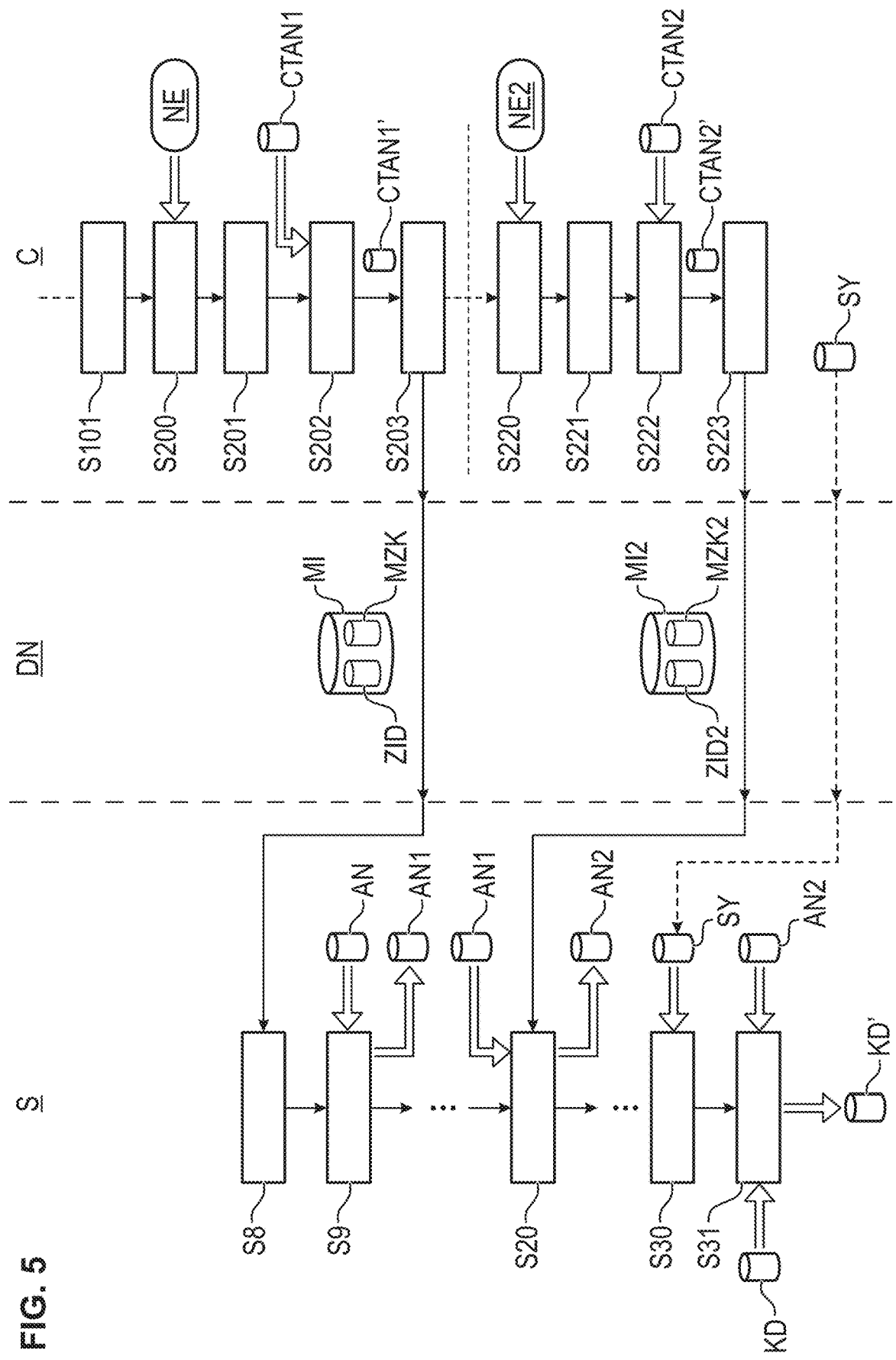
FIG. 5 shows further preferred steps for carrying out the image processing method.
Figure 10A:
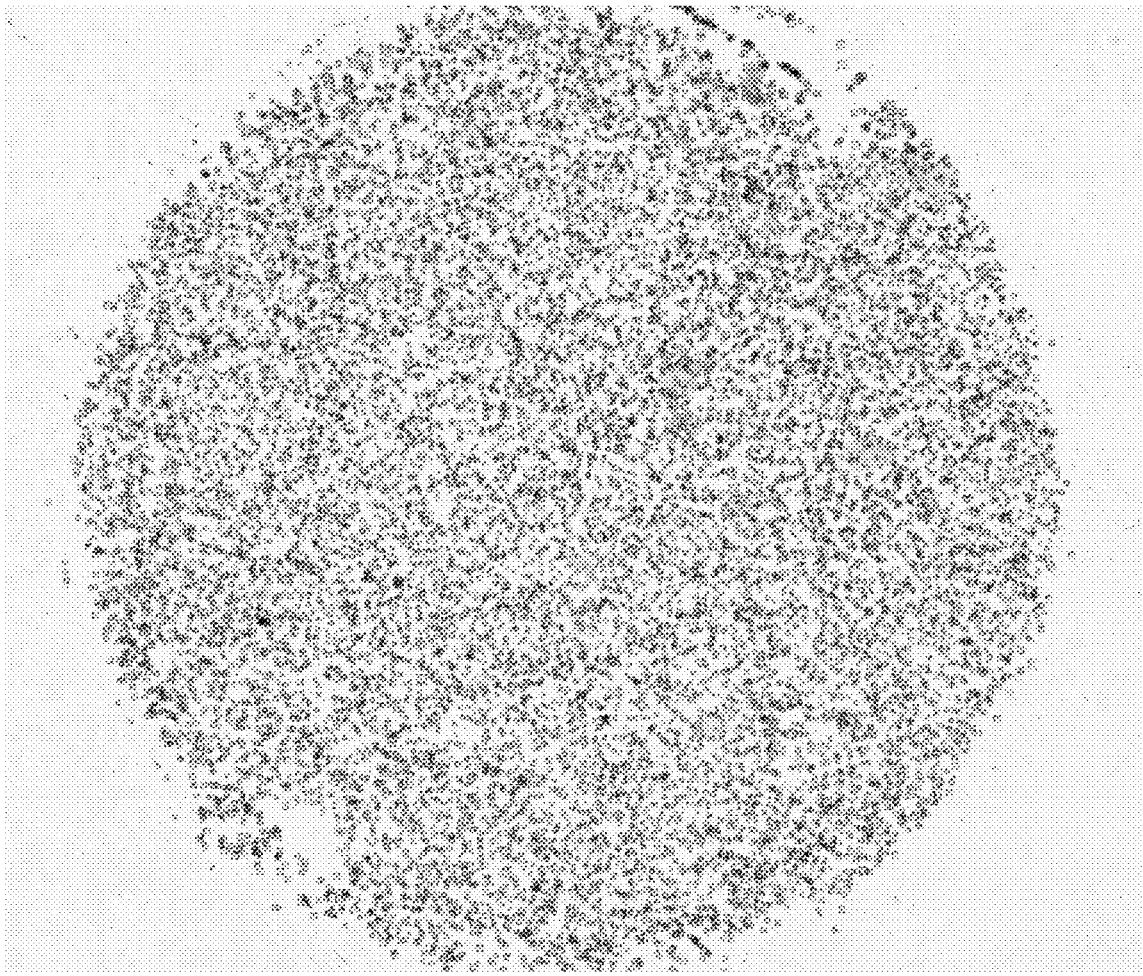
FIG. 10A shows the overall image of FIG. 8 together with optical markings of individual cell images.
Figure 10B:
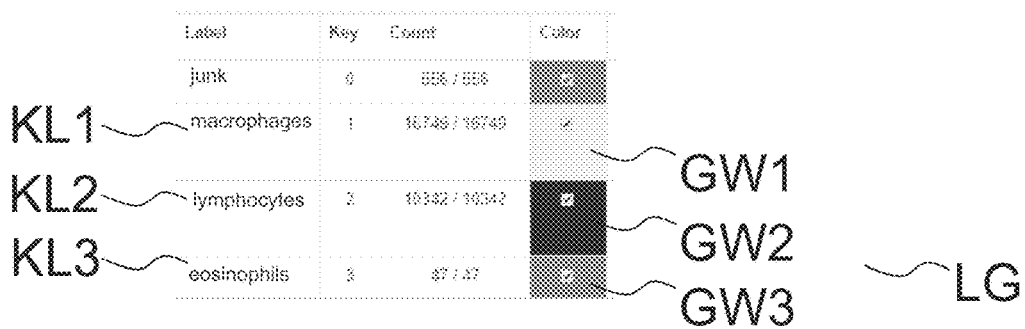
FIG. 10B shows a key for different greyscale levels of optical markings from FIG. 10A in relation to different cell classes.
Figure 13A:
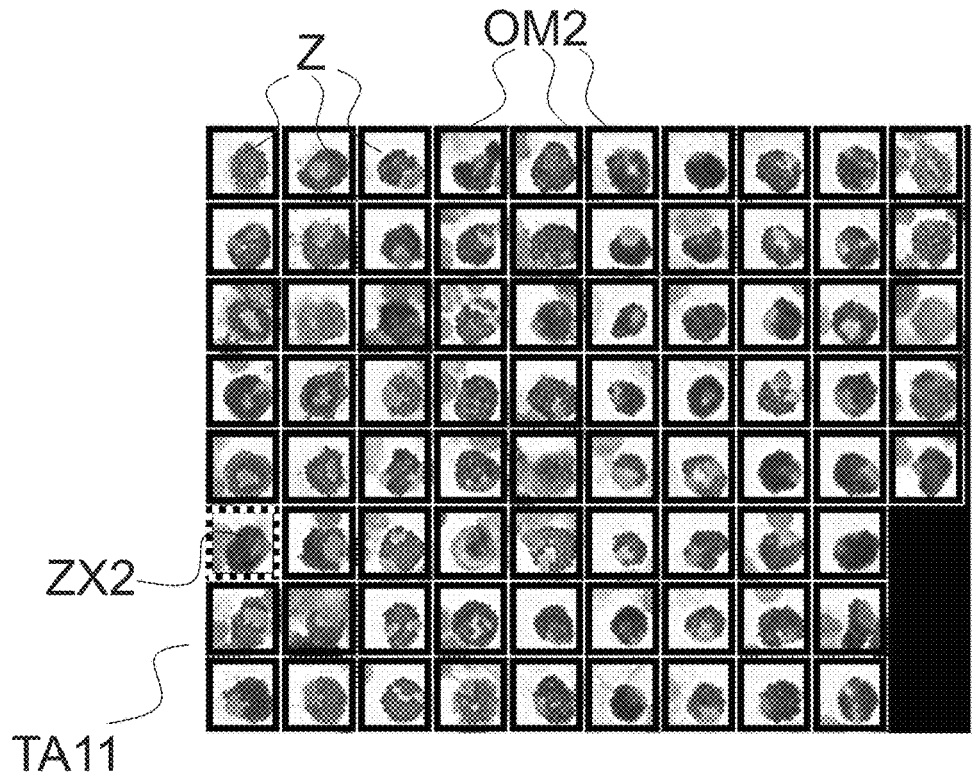
FIG. 13A shows another portion of another cell class or another class image, together with corresponding optical markings.
Figure 13B:
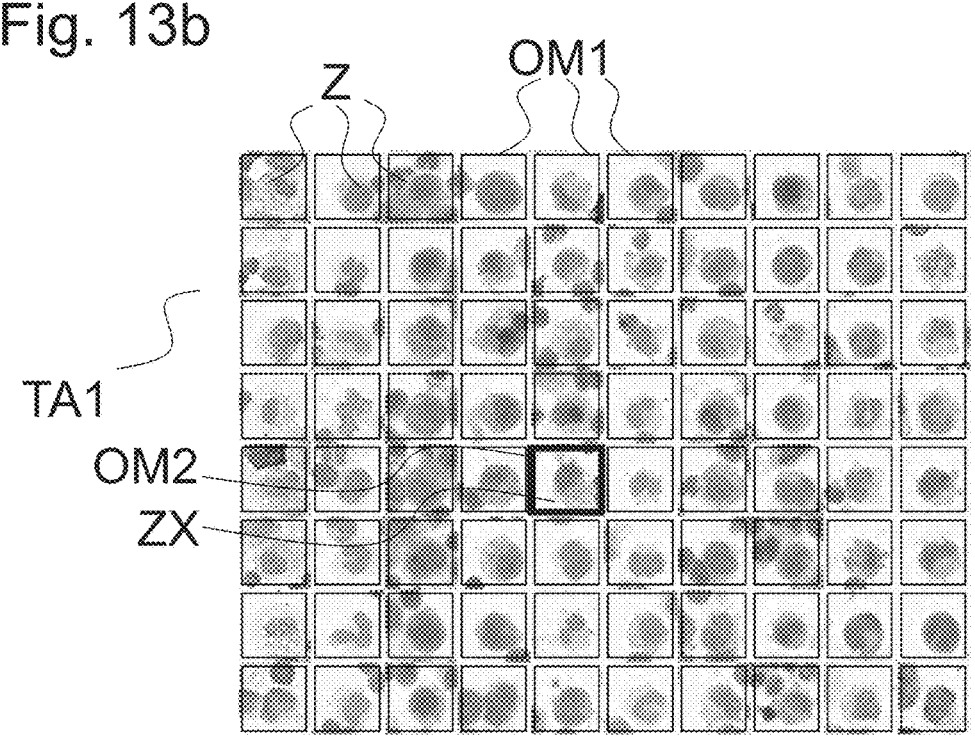
FIG. 13B shows the portion of FIG. 12A and a modified optical marking of an individual cell image.
Figure 14:
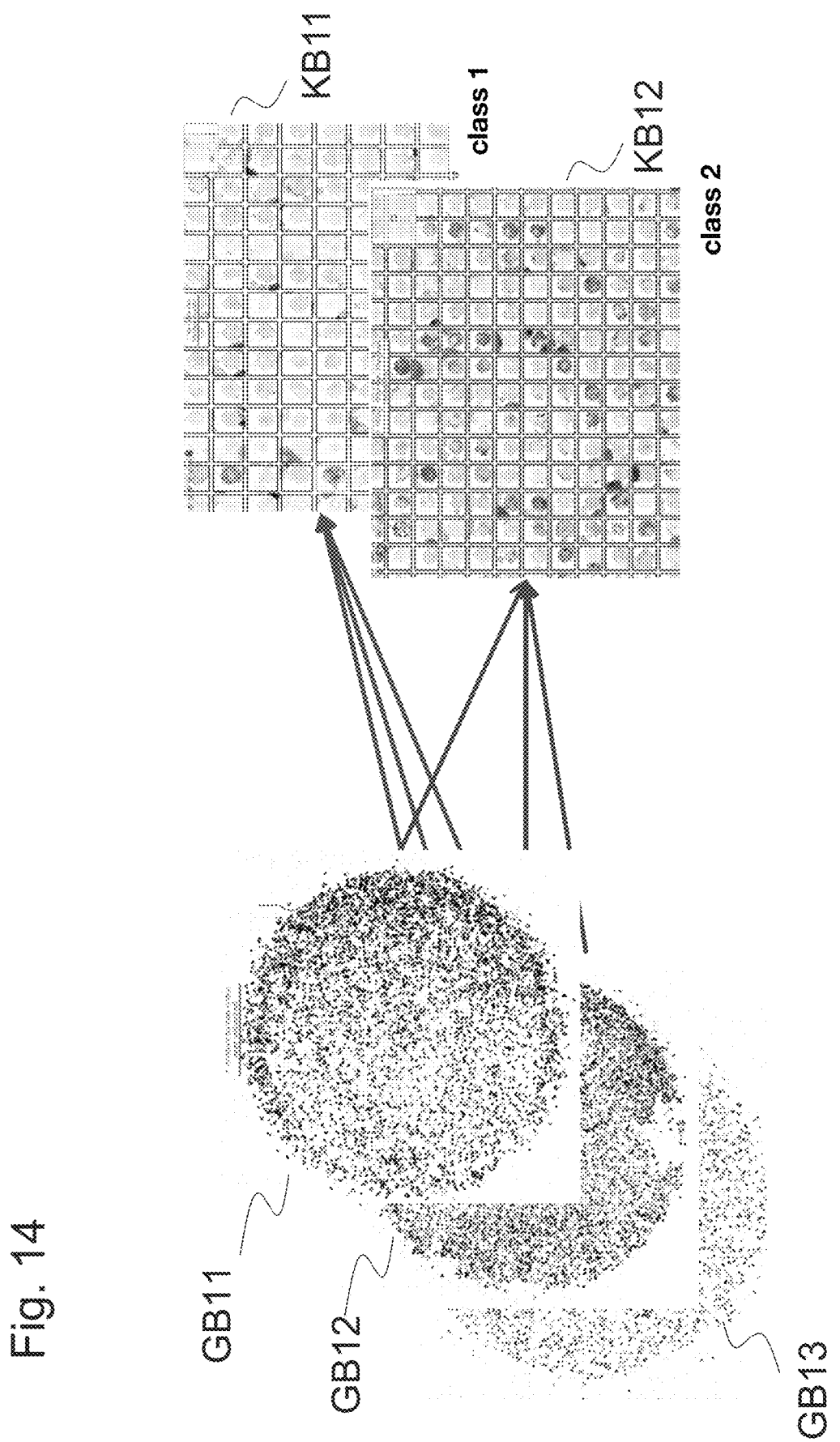
FIG. 14 shows a plurality of overall images with a plurality of class images.

FIG. 5 shows further preferred steps of a preferred embodiment of the proposed image processing method. The display step S101 of FIG. 4 is followed on the client side C by a step S200. In step S200, a user input NE is received, the latter indicating a selection of a displayed cell image, preferably a single displayed cell image. Further, the user input NE indicates a new mapping of the selected cell image to a modified cell class. To this end, FIG. 13B shows the portion TA1 with the above-described optical markings OM1, which indicate a mapping of the cells Z to the same cell class in accordance with the associated class image of the portion TA1. If a user selects a certain cell or a certain cell image ZX by means of a user input using a mouse or keyboard, for example, the user can further also indicate the cell class to which the cell ZX should be reclassified within the scope of the user input, for example by entering a number corresponding to a cell class number. Thus, the user indicates a modified cell class. Preferably, the modified cell class can be entered not by typing a number corresponding to a cell class number using the keyboard but instead by way of a selection by clicking a cell class KL1, KL2, KL3 from a key LG, as illustrated in exemplary fashion in FIG. 10B.

In FIG. 5, there is a step S201 in which the client then generates and also displays a new optical marking OM2 for the selected cell image ZX in correspondence with the modified cell class, as illustrated in FIG. 13B. However, the selected cell image ZX remains in the portion TA1 or the associated class image and is initially not removed therefrom. This is advantageous since the reclassification of the cell ZX undertaken here is subsequently displayed to a further pathologist when they observe the portion TA1 and they can check and possibly undo this reclassification. Thus, class mappings of a cell by a first pathologist on the client system can as a result subsequently be checked by a further pathologist client and can be undone where necessary.

To this end, the client modifies the temporarily stored partial annotation data record CTAN1 in a step S202, see FIG. 5, in correspondence with the selected cell image ZX and the modified cell class. Then, the modified or altered partial annotation data record CTAN1' is created. Information indicating the selected cell image ZX and the modified cell class is transmitted from the client to the server S via the data network DN in a step S203. To this end, the client C transmits modification information MI which includes identification data ZID which identify or indicate the selected cell or the selected cell image ZX. The modification information MI further includes the modified cell class in the form of the class identification data MZK.

Then, the server S receives the modification information MI in a step S8 and transitions into step S9. In step S9, the server modifies the annotation data record AN in correspondence with the received information MI or in correspondence with the selected cell image ZX in the modified cell class. Thus, the server S then generates the modified annotation data AN1.

Thus, a technical method is proposed, within the scope of which a user can carry out the technical task of classifying cell images to cell classes under continuous human-machine interaction and within the scope of which the user is assisted by the proposed exemplary embodiment of a method. Thus, the user only need select a cell image on the client and specify a modified cell class, wherein then it is not only the corresponding optical marking on the display of the client that is altered automatically but precisely also corresponding information that is transmitted to the server, the latter modifying the annotation data record stored there in correspondence with the selected cell image and the modified cell class. Thus, the server is used as a central system for tracking changes of a mapping of cell images to cell classes such that a central data record is available there, which continues to track the changes of mappings undertaken by a user at a client. To this end, it is not necessary to transmit the entire annotation data record from the server to the client and, following a modification, transmit the said annotation data record back accordingly but instead it is only information relating to the selected cell image and the modified cell class that is transmitted from the client back to the server. This minimizes data traffic during the transmission via the data network and consequently makes the former faster than in the case of an overall transmission of the annotation data record from the server to the client and back again.

On the client side, further steps can preferably be carried out on the client. These steps S220 to S223 can be carried out on the same client or else can be carried out at a later time on a different client. In a step S220, there is, in a manner analogous to step S200 described above, a reception of a user input NE2, which indicates a selection of a displayed cell image and which further indicates a mapping of the selected cell image to a modified cell class. By way of example, a further portion TA11, see FIG. 13A, of a different cell class or of a different cell image—or else of the same cell class or the same cell image—can be displayed on the client C or else on a different client at a corresponding later time. Then, in a subsequent step S221, a new optical marking can be generated and displayed for the selected cell image, for example the cell image ZX2 from FIG. 13A, on the client side, in a manner analogous to step S201 described above. In a step S222, which is analogous to step S202 described above, it is then possible on the client side to modify a temporarily stored partial annotation data record CTAN2 in correspondence with the selected or chosen cell image ZX2 and the modified cell class on the client in order, for example, to obtain the modified partial annotation data record CTAN2'. In a step S223, which is analogous to step S203 described above, modification information MI2 indicating the selected cell image ZX2 by means of information ZID2 and the modified cell class by means of the data MZK2 is then transmitted from the client to the server. On the side of the server S, it is then possible to modify the already modified annotation data AN1 in a step S20, in a manner analogous to step S9 described above, in correspondence with the modification data MI2 or in correspondence with the selected cell image ZX2 and the modified cell class in order to obtain the modified annotation data AN2.

Therefore, the exemplary embodiment described here is advantageous, in particular, since in this case and within a guided human-machine interaction the user can check and correct a check of the mapping of cell images to cell classes as carried out by the computer-assisted algorithm, wherein only a requested portion is in each case transferred from the server to the client and the optical markings on the client for this second portion are only generated and displayed after the transmission of the corresponding portion. Thus, the user need not receive an entire class image with the client but can do this by requesting portions in each case. Thus, within the scope of interactive searching of and requesting stored images, the user can more efficiently check and correct the classification task of mapping cell images to cell classes undertaken by the computer-assisted algorithm.

Then, a synchronization request SY can be received on the server S in a subsequent step S30. This synchronization request SY can preferably be received from a client system C via the data network DN. Following the reception of the synchronization request SY, the server synchronizes the classification data KD with the available modified annotation data AN2 in a step S31. As a result, synchronized classification data KD' are obtained. The advantage is that different users at different client systems C can check and modify a classification of cell images. Thus, a plurality of users on a plurality of client systems can modify the same annotation data record AN and it is possible to track the modification information in the modified annotation data record AN2. Only once the server S receives a corresponding synchronization request SY is the currently available modification of a mapping of cell images to cell classes synchronized back to the classification data record KD such that a modified classification data record KD' is obtained. This classification data record KD' can then be used to display altered optical markings for overall images, for example for the overall image GB11 of FIG. 10A.

Figure 6:
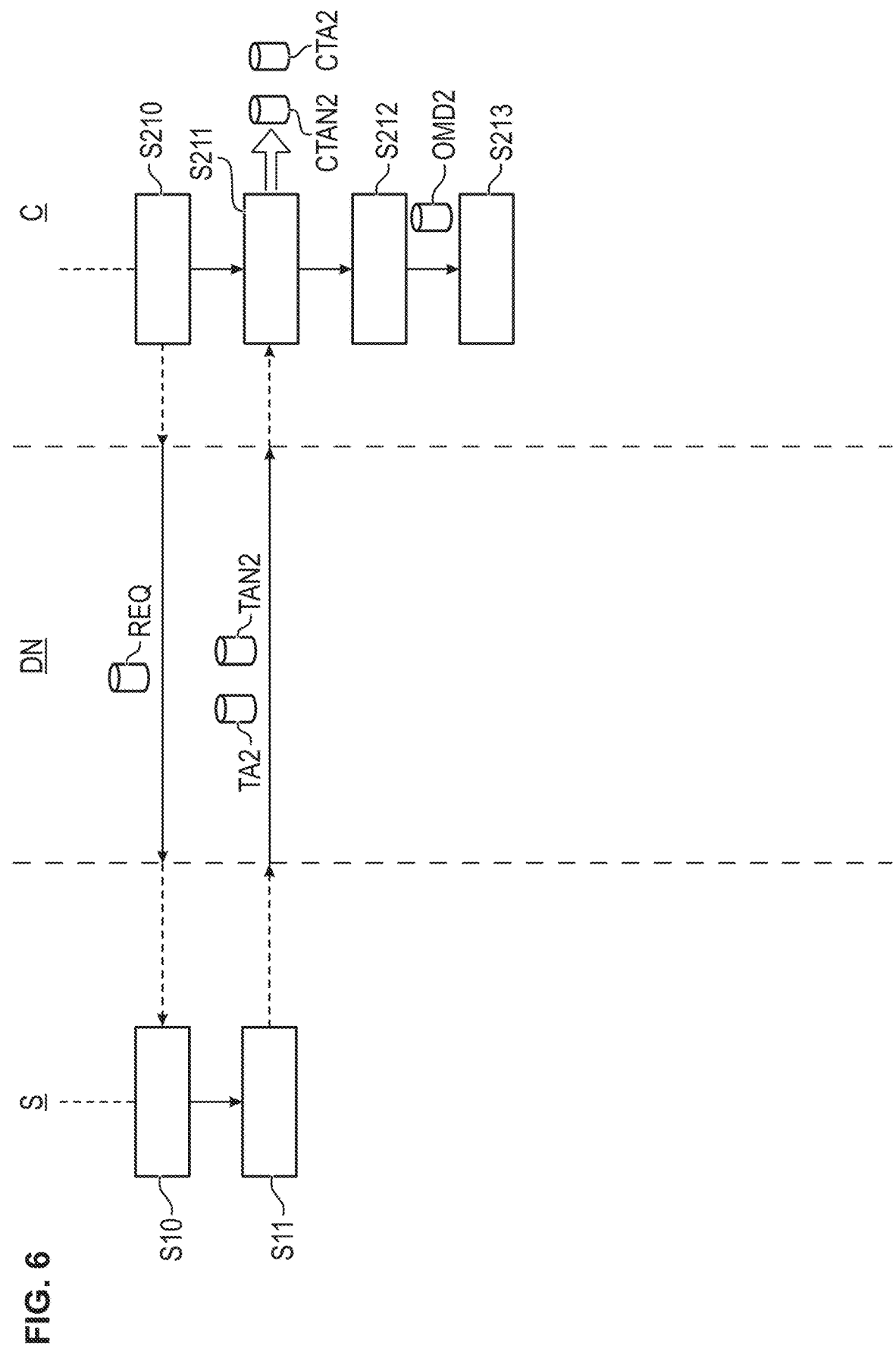
FIG. 6 shows, yet again, further preferred steps for carrying out the image processing method.

FIG. 6 shows preferred steps for carrying out a preferred exemplary embodiment of the proposed image processing method.

The server S is in a state according to the above-described step S9 or the above-described step S7. In a step S10, the server S expects a request notification or request information REQ. The client C is in a state according to the above-described step S203 or the above-described step S101. In a step S210, the client C sends the request notification REQ to the server S. Thus, as a result, the first client C requests a second portion of the class image. The client consequently requests the second portion of the class image from the server S.

The server S transmits further data after receiving the request notification REQ. In a step S11, the server S transmits the second portion TA2 and, further, at least a second partial annotation data record TAN2 corresponding to the second portion. This transmission of the second partial annotation data record TAN2 can also be implemented by virtue of the entire annotation data record AN being transmitted during the transmission of the first partial annotation data record TAN1 of FIG. 4 such that the second partial annotation data record TAN2 need not be transmitted from the server S to the client at the same time as the time at which the second portion TA2 is transmitted.

In a step S211, the client C temporarily stores the second partial annotation data record TAN2 as temporary data record CTAN2. Preferably, in step S211, the client C stores the second portion TA2 as temporary portion CTA2.

In a step S212, the client C generates respective optical markings for respective cell images of the second portion TA2 or CTA2, wherein the respective optical markings indicate respective mapping of the respective cell images to a cell class corresponding to the class image. These optical markings are then given by the optical marking data OMD2. In a step S213, the client displays the second portion TA2 or CTA2 and the associated optical markings OMD2. The exemplary embodiment described here is advantageous since the client C can request and then display a first portion TA1 not only at a first time, as illustrated in FIG. 4, but said client C can, at a further time, then also request a second portion TA2 of the same class image at a later time. Thus, a class image of a certain class need not be transferred completely from the server S to the client C in order to display at least a portion of this class image on the server S. The client C can receive successive portions from the server S via the data network DN such that there is a lower latency of the image data transfer than in the case of the complete transmission of an entire class image or else of all class images. Further, the client C can successively sequentially generate appropriate optical marking data OMD and OMD2 at different times and need not generate these optical marking data ad hoc for a whole class image. As a result thereof, there also is a lower latency for the generation and the display of the optical marking data of a certain portion.

Figure 7A:
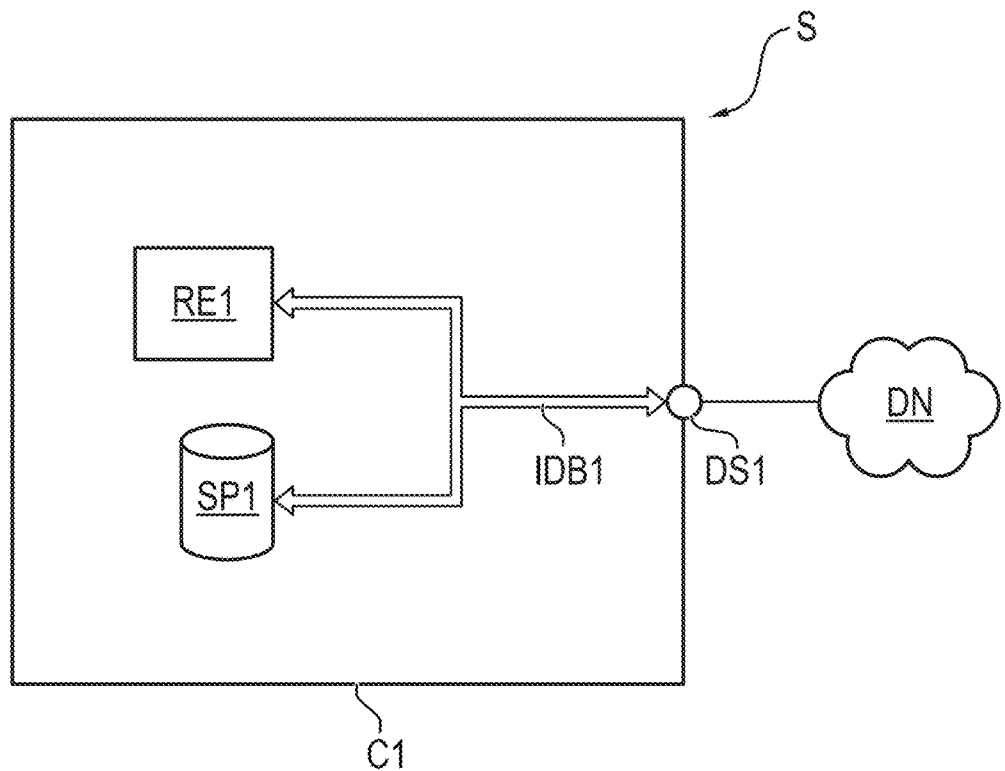
FIG. 7A shows a server.

FIG. 7A shows an exemplary server S. The server preferably has a data interface DS1 to a data network DN. The server S further has a computing unit RE1. The server further has a storage unit SP1. The server is preferably a computer C1. The data interface DS1 as well as the computing unit RE1 and the storage unit SP1 are preferably interconnected by way of an internal data bus IDB1.

Figure 7B:
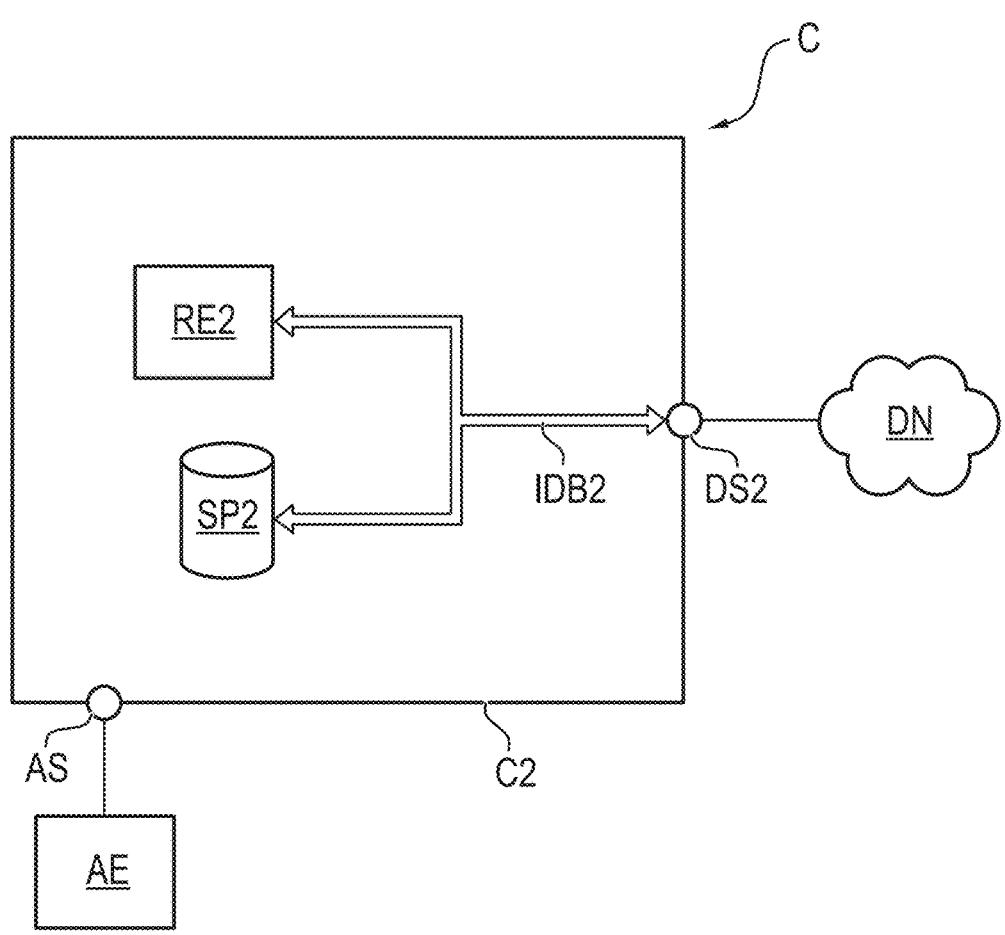
FIG. 7B shows a client.

FIG. 7B shows an exemplary client C. The client C has a data interface DS2 to a data network DN. The client C further has a computing unit RE2 and a storage unit SP2. The data interface DS2 and the computing unit RE2 as well as the storage unit SP2 are preferably interconnected by way of an internal data bus IDB2. The client C is preferably a computer C2. The client C preferably has an output interface AS to a display unit AE. Preferably, the display unit AE is an integral constituent part of the client C.

Figure 15A:
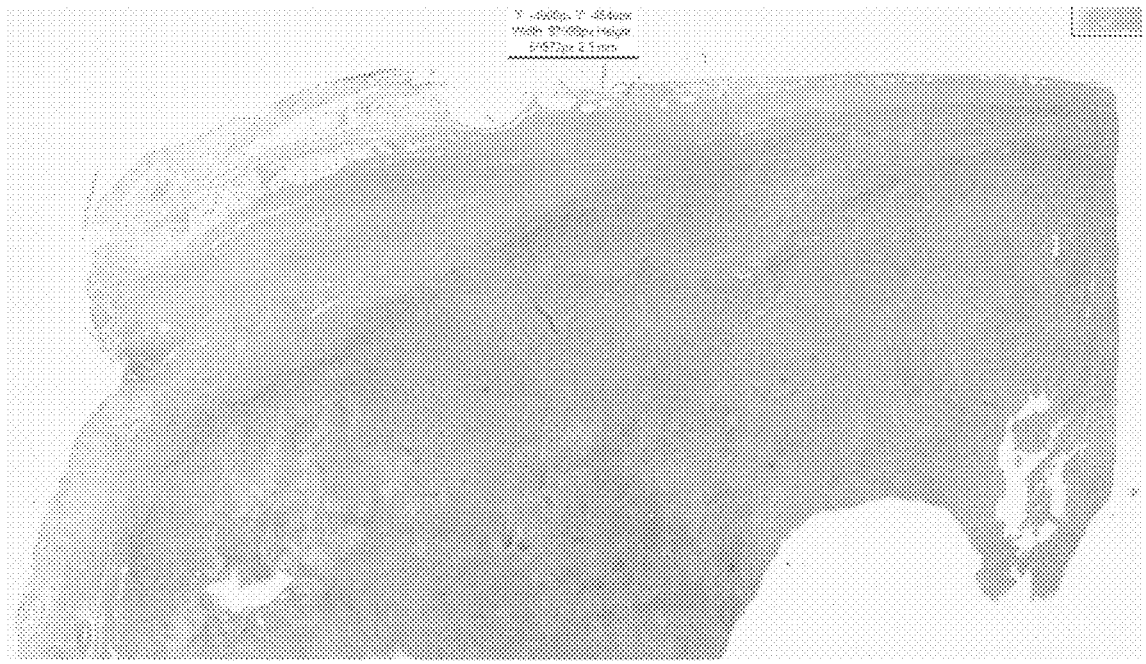
FIGS. 15a and 15b show overall images (GB21 and GB22, respectively), each representing a patient tissue sample in the form of a tissue section.
Figure 15B:
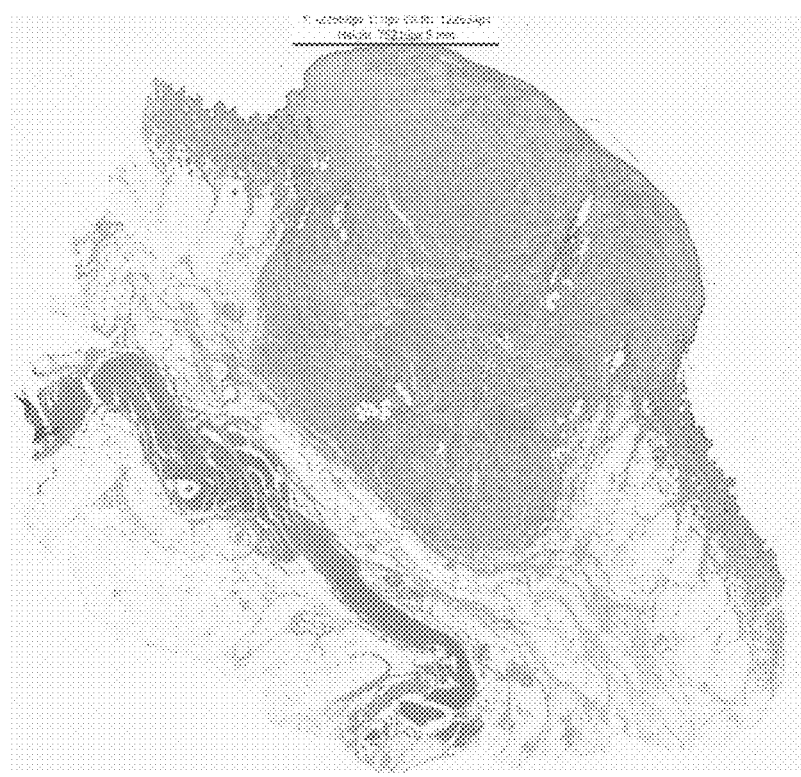
Figure 16A:
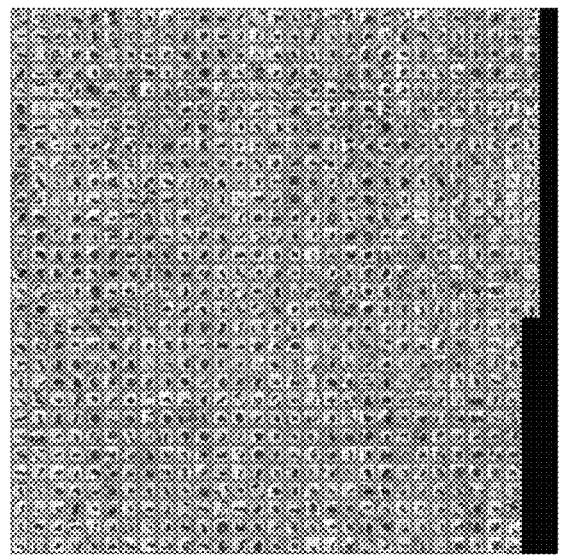
FIG. 16a shows an exemplary class image KB100 for the mitosis cell class.
Figure 16B:
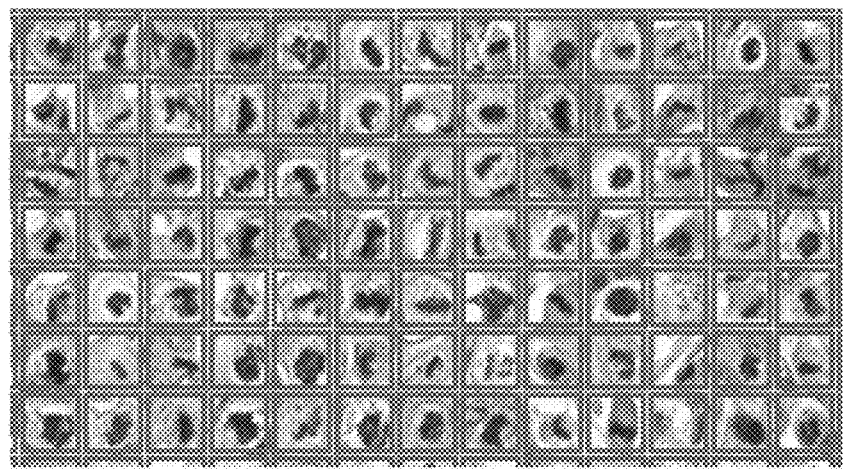
FIG. 16b shows an exemplary portion TA100 of the class image KB100 shown in FIG. 16a with cells of the mitosis cell class.
Figure 16C:
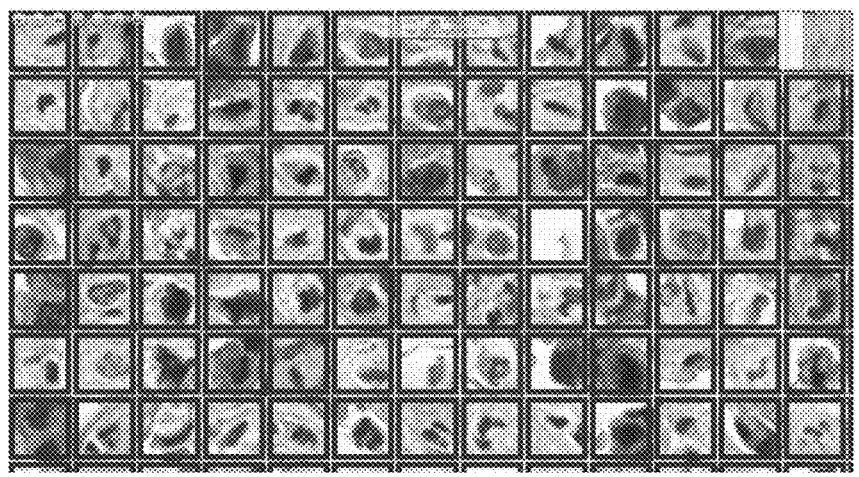
FIG. 16c shows an exemplary portion TA200 of the class image KB100 shown in FIG. 16a with cells of the non-mitosis cell class.

The explanations provided above were made with reference to overall images which each represent a patient cell sample in the form of a smear of a liquid patient sample; see, in particular, FIGS. 8, 9, 10, 11, 12 and 13. For the case where the overall images respectively represent a patient tissue sample in the form of a tissue section, FIGS. 15a and 15b show respective overall images GB21 and GB22, respectively. FIG. 16a shows an exemplary class image KB100 for the mitosis cell class. To this end, FIG. 16b shows an exemplary portion TA100 of the class image KB100 with cells of the mitosis cell class. FIG. 16c shows an exemplary portion TA200 for the non-mitosis cell class.

By looking at FIGS. 15 and 16, it is evident to a person skilled in the art that the proposed invention and its exemplary embodiments or embodiments can therefore also be carried out for overall images which respectively represent a patient tissue sample in the form of a tissue section.

Disclosed herein is also an image processing method to be carried out on a server S, which includes various steps: providing a plurality of overall images GB1, GB2, GB3, detecting individual cell images Z in the overall images GB1, GB2, GB3 by means of a computer-assisted algorithm, determining classification data KD by means of the computer-assisted algorithm, wherein the classification data KD indicate a respective unique mapping of a respective detected cell image Z to a respective cell class KL1, KL2, KL3, and wherein the classification data KD further have a respective measure of confidence in respect of the respective unique mapping, generating respective class images KB1 for the respective cell classes KL1, wherein a class image KB1 of a cell class KL1 of the cell images mapped to the cell class is chosen in a regular arrangement and with a predetermined order of the mapped cell images on the basis of the measures of confidence of the mapped cell images, generating an annotation data record AN, said annotation data record indicating for each class image respective mappings of the respective cell images to a cell class corresponding to the class image and further indicating respective local positions of the respective cell images within the class images, transmitting a portion TA1 of at least one class image KB1 and further at least one partial annotation data record TAN1 corresponding to the portion TA1 to a client C, receiving information from the client C indicating a selected cell image ZX and a modified cell class, and modifying the annotation data record AN in correspondence with the selected cell image ZX and the modified cell class.

Preferably, there is on the server S a reception of a synchronization request SY and a synchronization of the classification data KD with the modified annotation data record AN1, AN2.

Further disclosed herein is an image processing method to be carried out on a client C, including various steps of: requesting a portion TA1 of at least one class image KB1 from a server S, wherein a class image reproduces cell images mapped to a cell class in a regular arrangement and with a predetermined order, receiving the portion TA1 of the class image and further at least one partial annotation data record TAN1 corresponding to the portion TA1 from the server S and temporarily storing the partial annotation data record TAN1, wherein the partial annotation data record TAN1 for the portion TA1 of the class image indicates respective mappings of respective cell images Z to a cell class corresponding to the class image and wherein the partial annotation data record TAN1 indicates respective local positions of the respective cell images Z within the class image, generating respective optical markings OM1 for respective cell images of the portion on the basis of at least the partial annotation data record TAN1, wherein the respective optical markings OM1 indicate respective mappings of the respective cell images Z to a cell class corresponding to the class image, and displaying the portion TA1 and associated optical markings OM1 of cell images of the portion TA1. Preferably, the image processing method to be carried out on a client C further includes the steps of: receiving a user input NE, said user input indicating a selection of a displayed cell image ZX and further indicating a new mapping of the selected cell image ZX to a modified cell class, generating and displaying a new optical marking OM2 for the selected cell image ZX corresponding to the modified mapped cell class, modifying the temporarily stored partial annotation data record CTAN1 in correspondence with the selected cell image ZX and the modified cell class, transmitting information MI to the server indicating the selected cell image ZX and the modified cell class.

Further proposed is a computer program product comprising commands which, when the program is executed by a computer in the form of a server, prompt the latter to carry out the image processing method on the server S.

Further proposed is a computer program product comprising commands which, when the program is executed by a computer in the form of a client, prompt the latter to carry out the image processing method on the client C.

The features disclosed in the description above, the claims and the drawings can be of significance for the implementation of exemplary embodiments in their various configurations both on their own and in any combination and—provided nothing else emerges from the description—can be combined with one another as desired.

Although some aspects have been described in connection with a device, it is evident that said aspects are also a description of the corresponding method, and so a block or a component of a device can also be understood as a corresponding method step or as a feature of a method step. By analogy, aspects which have described in connection with a method step or as a method step are also a description of a corresponding block or detail or feature of a corresponding device.

Depending on particular implementation requirements, exemplary embodiments of the invention can be implemented in hardware form or in software form. Implementation can be achieved using a digital storage medium, for example a floppy disk, a DVD, a Blu-Ray Disc, a CD, a ROM, a PROM, an EPROM, an EEPROM or a FLASH memory, a hard disk or some other magnetic or optical memory, which stores electronically readable control signals which cooperate or can cooperate with a programmable hardware component such that the method in question is carried out.

A computing unit described herein can also be considered to be a hardware component in the form of a processor. A programmable hardware component can be formed by a processor, a central processing unit (CPU), a graphics processing unit (GPU), a computer, a computer system, an application-specific integrated circuit (ASIC), an integrated circuit (IC), a system on a chip (SOC), a programmable logic element or a field-programmable gate array with a microprocessor (FPGA).

A computer program product can be provided on a digital storage medium and can therefore be machine- or computer-readable. Some exemplary embodiments thus comprise a data medium having electronically readable control signals capable of cooperating with a programmable computer system or a programmable hardware component such that one of the methods described herein is carried out. Consequently, one exemplary embodiment is a data medium (or digital storage medium or computer-readable medium), on which the program for carrying out one of the methods described herein is stored.

In general, exemplary embodiments of the present invention can be implemented as a program, firmware, computer program or computer program product containing a program code or as data, the program code or the data being effective in carrying out one of the methods when the program runs on a processor or a programmable hardware component. By way of example, the program code or the data can also be stored on a machine-readable medium or data medium. The program code or the data can be available, inter alia, as source code, machine code or byte code or else as another intermediate code.

All references, including patents, patent applications and publications cited herein are incorporated herein by reference in their entirety and for all purposes to the same extent as if each individual publication or patent or patent application was specifically and individually indicated to be incorporated by reference in its entirety for all purposes.

What is claimed is:

1. An image processing system for displaying cells of a plurality of overall images, each respective overall image representing a respective patient tissue sample or a respective patient cell sample, the system comprising a server and furthermore a client in communication with the server via a data network:
   the server configured to:
      provide the overall images;
      detect individual cell images in the overall images by means of a computer-assisted algorithm;
      determine classification data by means of the computer-assisted algorithm,
         wherein the classification data indicate a respective unique mapping of a respective detected cell image to one of a plurality of cell classes, and
         wherein the classification data further have a respective measure of confidence in respect of the respective unique mapping; and
      generate respective class images for the respective cell classes,
         wherein a class image of a cell class reproduces the cell images mapped to the cell class in a regular arrangement and with a predetermined order, and
         wherein the order of the mapped cell images is chosen on the basis of the measures of confidence of the mapped cell images; and
   the server is further configured to:
      generate an annotation data record that indicates, for each class image:
         respective mappings of the respective cell images to a cell class corresponding to the class image; and
         respective local positions of the respective cell images within the class images; and
      receive, from the client, a request for a portion of a class image; and
      transmit, to the client, the portion and at least one partial annotation data record corresponding to the portion; and
   the client is further configured to:
      temporarily store the at least one partial annotation data record;
      generate respective optical markings for respective cell images of the portion on the basis of at least the partial annotation data record,
         wherein the respective optical markings indicate respective mappings of the respective cell images to a cell class corresponding to the class image; and
      display the portion and the associated optical markings on a display unit,
         wherein the portion comprises a plurality of cell images of overall images in respect of the mapping of the cell images to a certain cell class.

2. A system according to claim 1, wherein:
   the client is further configured to:

receive a user input indicating a selection of a displayed cell image and a new mapping of the selected cell image to a modified cell class;

generate and display a new optical marking for the selected cell image corresponding to the modified cell class;

modify the temporarily stored partial annotation data record in correspondence with the selected cell image and the modified cell class; and transmit, to the server, information indicating the selected cell image and the modified cell class; and the server is further configured to modify the annotation data record in correspondence with the selected cell image and the modified cell class.

3. A system according to claim 2, wherein:

the server is further configured to:

receive a second request for a second portion of the class image from the client; and transmit the second portion and at least one second partial annotation data record corresponding to the second portion to the client; and the client is further configured to:

temporarily store the second partial annotation data record;

generate respective optical markings for respective cell images of the second portion on the basis of at least the second partial annotation data record, wherein the respective optical markings indicate respective mappings of the respective cell images to a cell class corresponding to the class image; and display the second portion and associated optical markings on the display unit.

4. A system according to claim 2, wherein the server is further configured to:

receive a synchronization request; and synchronize the classification data with the modified annotation data record.

5. A system according to claim 1, wherein:

the server is further configured to:

receive a second request for a second portion of the class image from the client; and transmit the second portion and at least one second partial annotation data record corresponding to the second portion to the client; and the client is further configured to:

temporarily store the second partial annotation data record;

generate respective optical markings for respective cell images of the second portion on the basis of at least the second partial annotation data record, wherein the respective optical markings indicate respective mappings of the respective cell images to a cell class corresponding to the class image; and display the second portion and associated optical markings on the display unit.

6. An image processing method to be carried out on a server, the method comprising:

providing a plurality of overall images, wherein a respective overall image represents a respective patient tissue sample or a respective patient cell sample;

detecting individual cell images in the overall images by means of a computer-assisted algorithm;

determining classification data by means of the computer-assisted algorithm, wherein the classification data indicate a respective unique mapping of a respective detected cell image to a respective cell class, and wherein the classification data further have a respective measure of confidence in respect of the respective unique mapping;

generating respective class images for the respective cell classes, wherein a class image of a cell class of the cell images mapped to the cell class is chosen in a regular arrangement and with a predetermined order of the mapped cell images on the basis of the measures of confidence of the mapped cell images;

generating an annotation data record that indicates, for each class image:

respective mappings of the respective cell images to a cell class corresponding to the class image; and respective local positions of the respective cell images within the class images;

transmitting, to a client, a portion of at least one class image and at least one partial annotation data record corresponding to the portion;

receiving, from the client, information indicating a selected cell image and a modified cell class; and modifying the annotation data record in correspondence with the selected cell image and the modified cell class.

7. The image processing method according to claim 6, further comprising:

receiving a synchronization request; and synchronizing the classification data with the modified annotation data record.

8. An image processing method to be carried out on a client, the method comprising:

requesting, from a server, a portion of at least one class image, wherein a class image reproduces cell images mapped to a cell class in a regular arrangement and with a predetermined order;

receiving, from the server, the portion of the class image and at least one partial annotation data record corresponding to the portion, wherein the partial annotation data record for the portion of the class image indicates respective mappings of respective cell images to a cell class corresponding to the class image, and wherein the partial annotation data record indicates respective local positions of the respective cell images within the class image;

temporarily storing the partial annotation data record;

generating respective optical markings for respective cell images of the portion on the basis of at least the partial annotation data record, wherein the respective optical markings indicate respective mappings of the respective cell images to a cell class corresponding to the class image; and displaying the portion and associated optical markings of cell images of the portion.

9. An image processing method according to claim 8, further comprising:

receiving a user input indicating a selection of a displayed cell image and a new mapping of the selected cell image to a modified cell class;

generating and displaying a new optical marking for the selected cell image corresponding to the modified mapped cell class;

modifying the temporarily stored partial annotation data record in correspondence with the selected cell image and the modified cell class; and transmitting information to the server indicating the selected cell image and the modified cell class.

\* \* \* \* \*